United States Patent
Zouaghi

(10) Patent No.: US 11,969,361 B2
(45) Date of Patent: Apr. 30, 2024

(54) ADJUSTABLE TIBIAL TRIAL INSERT

(71) Applicant: Aesculap AG, Tuttlingen (DE)

(72) Inventor: Housseyn Zouaghi, Chaumont (FR)

(73) Assignee: Aesculap AG, Tuttlingen (DE)

( * ) Notice: Subject to any disclaimer, the term of this patent is extended or adjusted under 35 U.S.C. 154(b) by 239 days.

(21) Appl. No.: 17/545,243

(22) Filed: Dec. 8, 2021

(65) Prior Publication Data
US 2022/0175553 A1     Jun. 9, 2022

(30) Foreign Application Priority Data
Dec. 9, 2020 (EP) .................................. 20212707

(51) Int. Cl.
*A61F 2/46*     (2006.01)
*A61F 2/30*     (2006.01)

(52) U.S. Cl.
CPC .. *A61F 2/4684* (2013.01); *A61F 2002/30537* (2013.01); *A61F 2002/4661* (2013.01)

(58) Field of Classification Search
None
See application file for complete search history.

(56) References Cited

U.S. PATENT DOCUMENTS

| 2006/0111790 | A1* | 5/2006 | Dietz | ..................... | A61F 2/4684 |
| | | | | | 623/20.32 |
| 2010/0063595 | A1 | 3/2010 | Dietz | | |
| 2010/0250571 | A1 | 9/2010 | Pierce et al. | | |
| 2013/0023794 | A1 | 1/2013 | Stein et al. | | |
| 2017/0065438 | A1 | 3/2017 | Burnikel | | |
| 2020/0155135 | A1 | 5/2020 | Cole et al. | | |

FOREIGN PATENT DOCUMENTS

WO     2019115744 A1     6/2019

OTHER PUBLICATIONS

Search Report received in European Application No. 20212707.2-1122 dated Apr. 23, 2021, 8 pages.

* cited by examiner

*Primary Examiner* — Brian A Dukert
*Assistant Examiner* — Melissa A Hoban
(74) *Attorney, Agent, or Firm* — Christopher A. Rothe; Culhane Meadows PLLC

(57) ABSTRACT

A tibial trial insert includes an upper plate and lower plate. An adjustment arrangement between the upper and lower plates is actuatable to adjust a gap between the upper and lower plates. The adjustment arrangement includes a first lift with a first lever arm arrangement and a second lift with a second lever arm arrangement. Each lever arm arrangement is indirectly connected to the upper and lower plates and pivotally movable to vary its length and adjust the gap between the upper and lower plates. The first lift includes an actuator coupled to the first lever arm arrangement. Actuation of the actuator varies the length of the first lever arm arrangement. The adjustment arrangement includes a coupling that couples the second lift to the first lift and configured such that the length of the second lever arm arrangement is varied synchronously to the first lever arm arrangement.

9 Claims, 9 Drawing Sheets

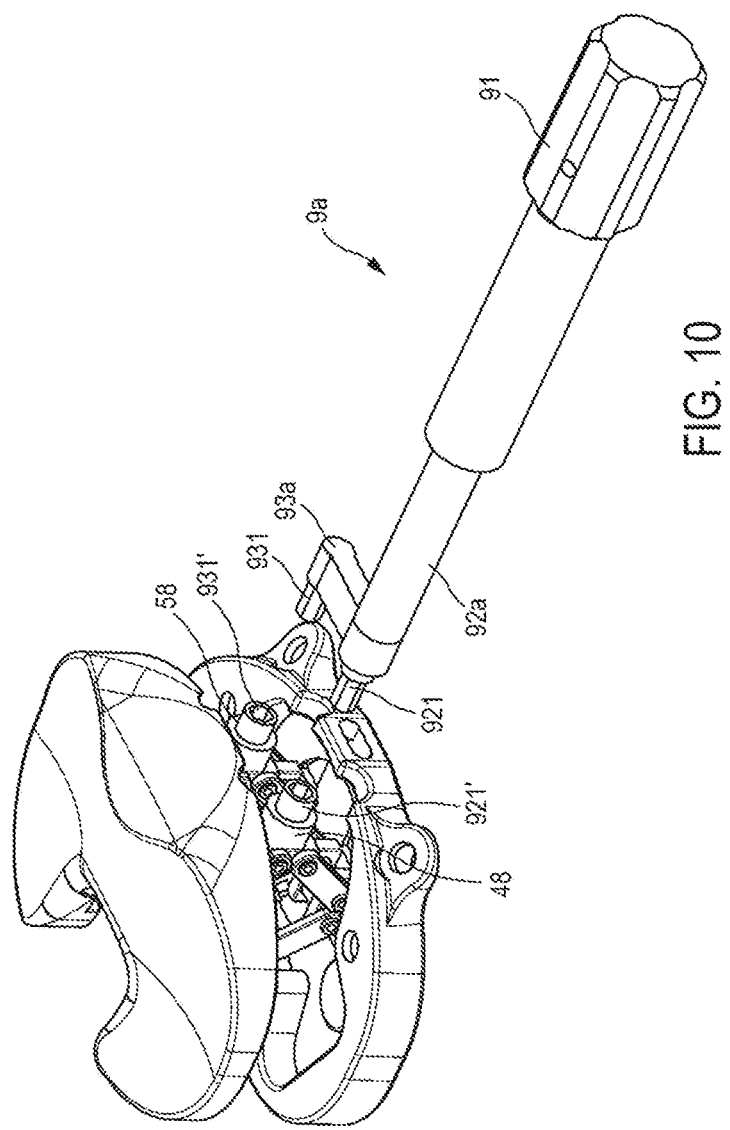

ADJUSTABLE TIBIAL TRIAL INSERT

CROSS-REFERENCE TO RELATED APPLICATIONS

This application claims priority to European Application No. 20212707.2, filed Dec. 9, 2020, the content of which is incorporated by reference herein in its entirety.

FIELD

The invention relates to an adjustable tibial trial insert, comprising: an upper plate including an upper articular surface configured for articulation with a femoral surface; a lower plate positioned below the upper plate along an adjustment axis and including a lower surface configured for tibial fixation; an adjustment arrangement arranged between the upper plate and the lower plate and actuatable for adjustment of a gap between the upper plate and the lower plate along the adjustment axis; wherein the adjustment arrangement comprises at least a first scissor lift mechanism with a first lever arm arrangement and a separate second scissor lift mechanism with a second lever arm arrangement, wherein each of the lever arm arrangements is at least indirectly connected to the upper plate and the lower plate, and wherein each of the lever arm arrangements is pivotally movable between different positions for variation of its length along the adjustment axis in order to adjust the gap between the upper plate and the lower plate.

BACKGROUND

Such an adjustable tibial trial insert is known from WO 2019/115744 A1 and comprises a first plate coupled to a second plate by an adjustment arrangement including a plurality of adjustors. The adjustors are actuatable to vary a vertical gap between the first and second plates. The plurality of adjustors consists of three adjustors arranged in a triangular configuration, wherein each adjustor comprises a scissor lift mechanism. In order to adjust the gap between the upper plate and the lower plate each of the three scissor lift mechanisms is separately actuatable by means of separate actuator bolts.

Similar adjustable tibial trial inserts are known from US 2017/0065438 A1 and US 2010/0063595 A1. However, the tibial trial inserts disclosed in these documents each comprise only a single scissor lift mechanism for adjusting the gap between the upper and the lower plates.

SUMMARY

It is an objective of the present invention to provide an adjustable tibial trial insert that avoids adjustment-related deformations of the upper plate and the upper articular surface and allows a simple and stable adjustment of the gap between the upper plate and the lower plate.

This objective is solved in that the first scissor lift mechanism comprises an actuator element coupled to the first lever arm arrangement and configured such that actuation of the actuator element varies the length of the first lever arm arrangement; and that the adjustment arrangement comprises at least one coupling element coupling the second scissor lift mechanism to the first scissor lift mechanism and configured such that the length of the second lever arm arrangement is varied synchronously to the first lever arm arrangement. By means of the solution according to the invention, the second scissor lift mechanism is kinematically coupled to the first scissor lift mechanism. For that purpose, the coupling element is provided. The coupling element is connected to both the first scissor lift mechanism and the second scissor lift mechanism and produces a force and motion transmitting connection and/or coupling. In other words, the second lever arm arrangement is coupled to the first lever arm arrangement and positively driven by the coupling element. As a result, an actuation of the actuator element of the first scissor lift mechanism causes not only a variation of the length of the first lever arm arrangement, but at the same time a synchronous variation of the length of the second lever arm arrangement retraced via the coupling element. In other words, the first lever arm arrangement is extendable and retractable along the adjustment axis by means of actuating the actuator element. In contrast to the case of a separate adjustment of each one of the scissor lift mechanisms, an unintentional deformation or even damage of the upper plate and/or the upper articular surface may be prevented thereby. Preferably, the second scissor lift mechanism does not include a respective actuator element so that the length of the second lever arm arrangement is variable exclusively indirectly, namely via the kinematic positive guide on the first lever arm arrangement. Preferably, the first scissor lift mechanism and the second scissor lift mechanism have identical movement kinematics. In other words, the first lever arm arrangement and the second lever arm arrangement have an identical design, preferably a completely identical design, at least in relation to an arrangement and/or configuration of the corresponding lever arms. Preferably, the adjustment axis is a vertical axis. Preferably, the adjustment arrangement includes exactly two scissor lift mechanisms, namely the first and the second scissor lift mechanism.

In one embodiment, the first scissor lift mechanism and the second scissor lift mechanism are spaced apart from each other along a longitudinal axis, wherein the longitudinal axis is oriented perpendicular to the adjustment axis. Owing to the spaced arrangement of the two separate scissor lift mechanisms perpendicular to the adjustment axis, a particularly stable support of the upper plate is facilitated during adjustment of the gap along the adjustment axis. In this embodiment of the invention, the coupling element extends along the longitudinal axis between the first scissor lift mechanism and the second scissor lift mechanism.

In one embodiment, the first scissor lift mechanism and the second scissor lift mechanism are arranged in an in-line configuration and/or are arranged symmetrically with respect to a center plane of the upper plate. As a result, in particular a further improved stability of the adjustment mechanism and, thus, also the entire tibial trial insert can be achieved. Preferably, the central plane is a vertical central transverse plane of the upper plate and/or the tibial trial insert. Preferably, the first scissor lift mechanism and the second scissor lift mechanism are designed essentially, preferably completely, symmetrical to each other in relation to the central plane. Preferably, the actuator element of the first scissor lift mechanism is excluded therefrom to the extent that the second scissor lift mechanism preferably does not include a respective actuator element.

In one embodiment the at least one coupling element extends from a first end to a second end, wherein the first end is coupled to a lever of the first lever arm arrangement and the second end is coupled to a respective lever of the second lever arm arrangement. As a result, in particular a structurally simple and yet robust kinematic coupling between the first lever arm arrangement and the second lever arm arrangement is achieved. The first end of the coupling element is preferably coupled in a force-fitting, form-fitting and/or material-bonding engagement to said lever of the first lever arm arrangement. Preferably, the same applies accordingly to the coupling of the second end. Displacement of the first lever arm arrangement caused by actuation of the actuator element is transferred to the coupling element via the lever of the first lever arm arrangement connected to the coupling element and from there on to the lever of the second lever arm arrangement coupled to the coupling element. In connection with this embodiment of the invention, it is particularly advantageous if the first and the second lever arm arrangements have an at least essentially, preferably completely, identical design and/or include levers of identical arrangement and dimensions.

In one embodiment each of the lever arm arrangements comprises a plurality of inner lever arms and a plurality of outer lever arms, wherein the inner lever arms are disposed and pivotally movable in a first plane whose normal vector is oriented perpendicular to the adjustment axis, and wherein the outer lever arms are disposed and pivotally movable in a second plane spaced parallel to the first plane. In other words, the first lever arm arrangement comprises a plurality of first inner lever arms and a plurality of first outer lever arms, and the second lever arm arrangement comprises a plurality of second inner lever arms and a plurality of second outer lever arms. The inner lever arms and the outer lever arms of each of the lever arm arrangements are disposed in different planes, namely the first plane and the second plane. Consequently, there are two first planes and two second planes provided, wherein one of the first planes is associated to the first lever arm arrangement and a further one of the first planes is associated to the second lever arm arrangement. The same applies in relation to the allocation of the two second planes. The inner and the outer lever arms have a longitudinal extension in the respective plane. This configuration of the lever arm arrangements produces a further improved stability of the adjustment arrangement during adjustment of the gap between the upper and the lower plate. Preferably, the coupling element is coupled to an inner lever arm of the first scissor lift mechanism and to a corresponding inner lever arm of the second scissor lift mechanism.

In one embodiment, each of the plurality of inner lever arms and each of the plurality of outer lever arms consist of four lever arms including two upper lever arms and two lower lever arms positioned below the two upper lever arms along the adjustment axis; each of the upper lever arms extending from a first end to a second end, the first ends of the upper lever arms being pivotally coupled to the upper plate; each of said lower lever arms extending from a first end to a second end, the first ends of the lower lever arms being pivotally coupled to the lower plate; each of the scissor lift mechanisms comprises a first coupling block and a second coupling block, each of the coupling blocks being disposed between the first plane and the second plane, wherein the second ends of the upper arms and the second ends of the lower arms are each pivotally coupled to one of the coupling blocks; the actuator element is threadably connected to the first coupling block and to the second coupling block of the first scissor lift mechanism along a transversal axis being oriented perpendicular to the adjustment axis such that the actuation of the actuator element translates the coupling blocks relative to each other to thereby vary the length of the first lever arm arrangement, wherein the variation of the length of the first lever arm arrangement is synchronously transmitted to the second lever arm arrangement by means of the coupling element. The upper lever arms are each, on their first end, coupled to the upper plate at least indirectly for pivot movement. The lower lever arms are each, on their first end, coupled to the lower plate at least indirectly for pivot movement. The second ends of the upper lever arms and the second ends of the lower lever arms facing each other and are mounted on the coupling blocks for pivot movement. Preferably, the first coupling block and the second coupling block are disposed spaced apart from each other along the transverse axis. The actuator element has a longitudinal extension along the transverse axis between a first end and a second end, wherein the first end and the second end are each threaded, and wherein the two threads are configured in opposite directions to each other. The first end and the second end of the actuator element interact with the first coupling block and the second coupling block, respectively, in threaded motion. For that purpose, the two coupling blocks each include a threaded hole provided with a complementary thread. As a result, a rotary actuation of the actuator element directed around the transverse axis causes the first coupling block and the second coupling block of the first scissor lift mechanism to be displaced relative to each other in translational movement along the transverse axis. As a result, the second ends of the upper and lower lever arms of the first lever arm arrangement are moved towards each other or away from each other along the transverse axis. Finally, as a result thereof, the length of the first lever arm arrangement is varied along the adjustment axis. Said variation is transferred synchronously to the second lever arm arrangement by means of the coupling element.

In one embodiment, the adjustment arrangement comprises a guiding bolt slidably connected to the first coupling block and the second coupling block of the second scissor lift mechanism along the transversal axis such that the coupling blocks of the second scissor lift mechanism are supported on the guiding bolt. Simply put, the second scissor lift mechanism includes said guiding bolt instead of an actuator element. Said guiding bolt cooperates with the coupling blocks and supports the latter during a force-guided length variation of the second lever arm arrangement. As a result, a further improved stability of the adjustment arrangement and a kinematically precise force guiding of the second scissor lift mechanism may be achieved. The guiding bolt has a longitudinal extension along the transverse axis. For sliding connection to the guiding bolt, the two coupling blocks each include a complementary bolt seat into which the guiding bolt is fitted. In contrast to the actuator element of the first scissor lift mechanism, the guiding bolt does not present any thread or the like for transmission of force and/or motion for the purpose of length adjustment of the second lever arm arrangement.

In one embodiment, the adjustment arrangement comprises a handle having a manipulation element operatively connected to the actuator element such that manipulation of the manipulation element actuates the actuator element to thereby vary the length of the lever arm arrangements in order to vary the gap between the upper plate and the lower plate. The handle is intended for easy handling of the adjustment arrangement and for ergonomic operation of the actuator element. For that purpose, the handle has a manipulator element which may be embodied in particular as a handwheel, rotary knob or the like. The manipulator element is connected to the actuator element in a force and motion transmitting manner such that a manual movement of the manipulator element causes an actuation of the actuator element for variation of the gap between the upper and the lower plate. The manipulation element can be permanently or detachably connected to the actuator element.

In one embodiment, the guiding bolt has a first portion slidably connected to the coupling blocks of the second scissor lift mechanism and a second portion fixedly connected to the handle. The first portion and the second portion are spaced apart from each other along a longitudinal axis of the guiding bolt. The first portion interacts with the coupling blocks, preferably with bolt seats of the coupling blocks, in sliding movement. The second portion is operatively connected to the handle. Owing to said connection of the guiding bolt to the handle, the second scissor lift mechanism is advantageously supported on the handle. The handle can be permanently or detachably connected to the second portion.

In one embodiment, the handle is detachably connected to the actuator element and/or the guiding bolt. As a result, the handle is removable, once the gap between the upper plate and the lower plate has been adjusted as desired. The detachable connection is preferably achieved by means of a plug connection between the manipulation element and the actuator element and/or the second portion of the guiding bolt.

In one embodiment, the adjustment arrangement comprises an upper connector portion for releasable form-fitting connection with a complementary connector portion of the upper plate and a lower connector portion for releasable form-fitting connection with a complementary connector portion of the lower plate. As a result, the adjustment arrangement can be connected to the upper and the lower plates without using a tool, as required. For that purpose, the corresponding connector portions are configured for releasable form-fitting connection. Preferably, the upper connector portion has a first partial section and a second partial section, wherein the first partial section is disposed and/or formed on an upper side of the first scissor lift mechanism and the second partial section on an upper side of the second scissor lift mechanism. Preferably, the same applies accordingly in relation to the configuration of the lower connector portion. As an alternative, the upper and the lower connector portions can each be embodied contiguous in one piece. The complementary connector portion of the upper plate is preferably disposed and/or formed on an inner side of the upper plate facing the lower plate. The complementary connector portion of the lower plate is preferably disposed and/or formed on an upper side of the lower plate facing the upper plate.

BRIEF DESCRIPTION OF THE DRAWING FIGURES

In the following, an embodiment of the invention will be described in detail with reference to the drawings. Throughout the drawings, the same elements will be denoted by the same reference numerals.

FIG. 10 is a variant of the tibial trial insert according to FIGS. 1 to 3, wherein the adjustment arrangement comprises a detachable handle.

DETAILED DESCRIPTION

Figure 1:
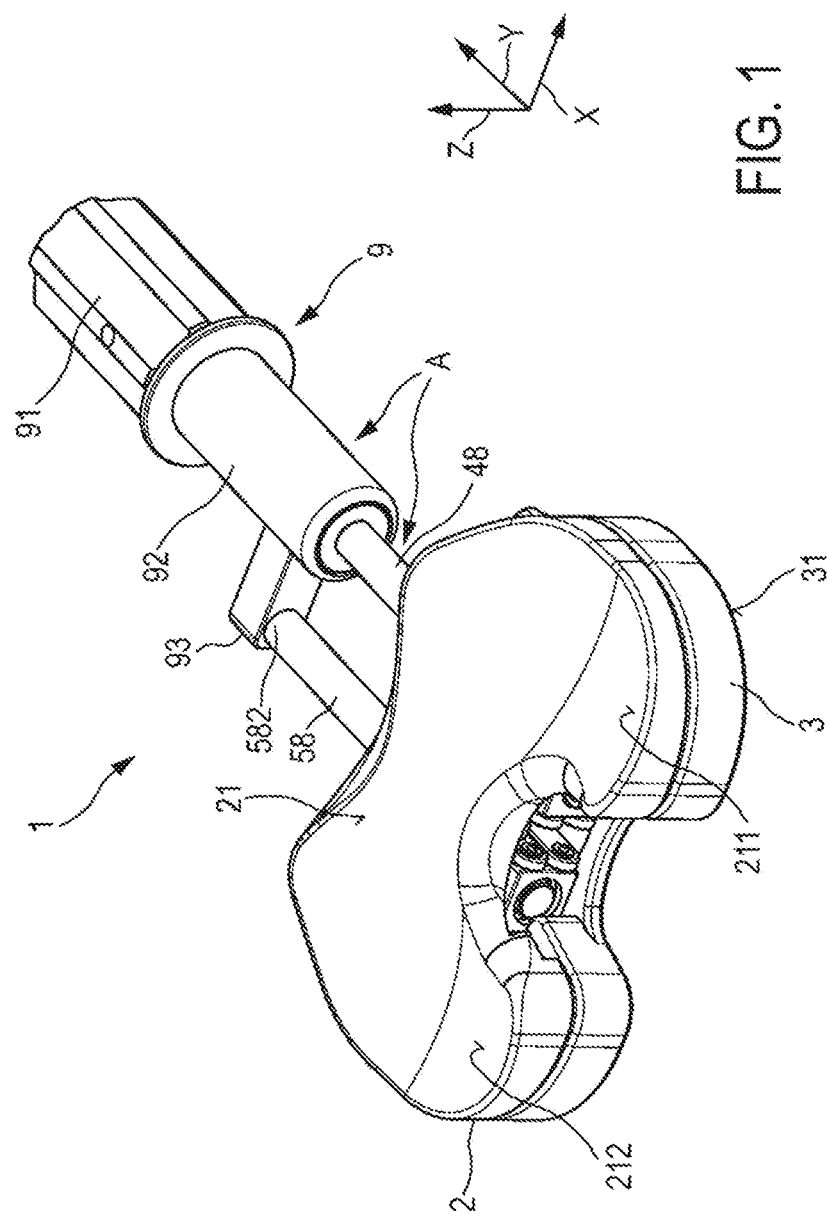
FIG. 1 is a perspective view of an adjustable tibial trial insert according to an embodiment, comprising an upper plate, a lower plate and an adjustment arrangement.
Figure 2:
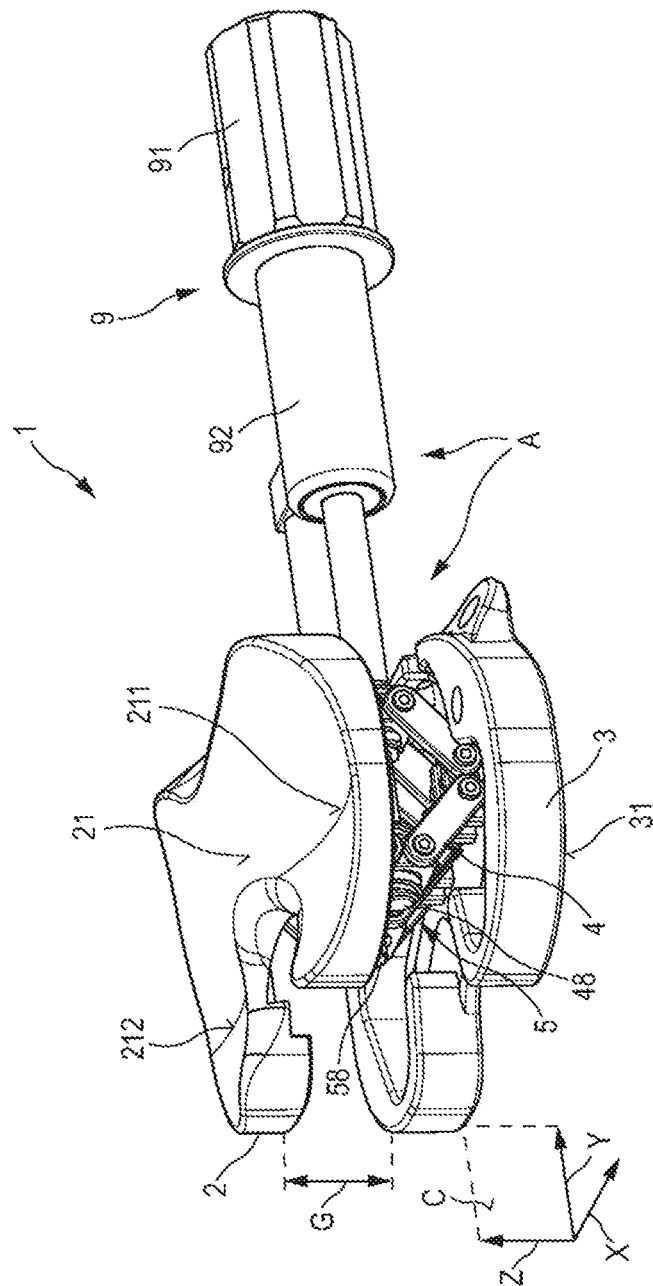
FIG. 2 is a further perspective view of the tibial trial insert according to FIG. 1, wherein the upper plate and the lower plate are spaced apart from each other by a gap adjusted using the adjustment arrangement.
Figure 3:
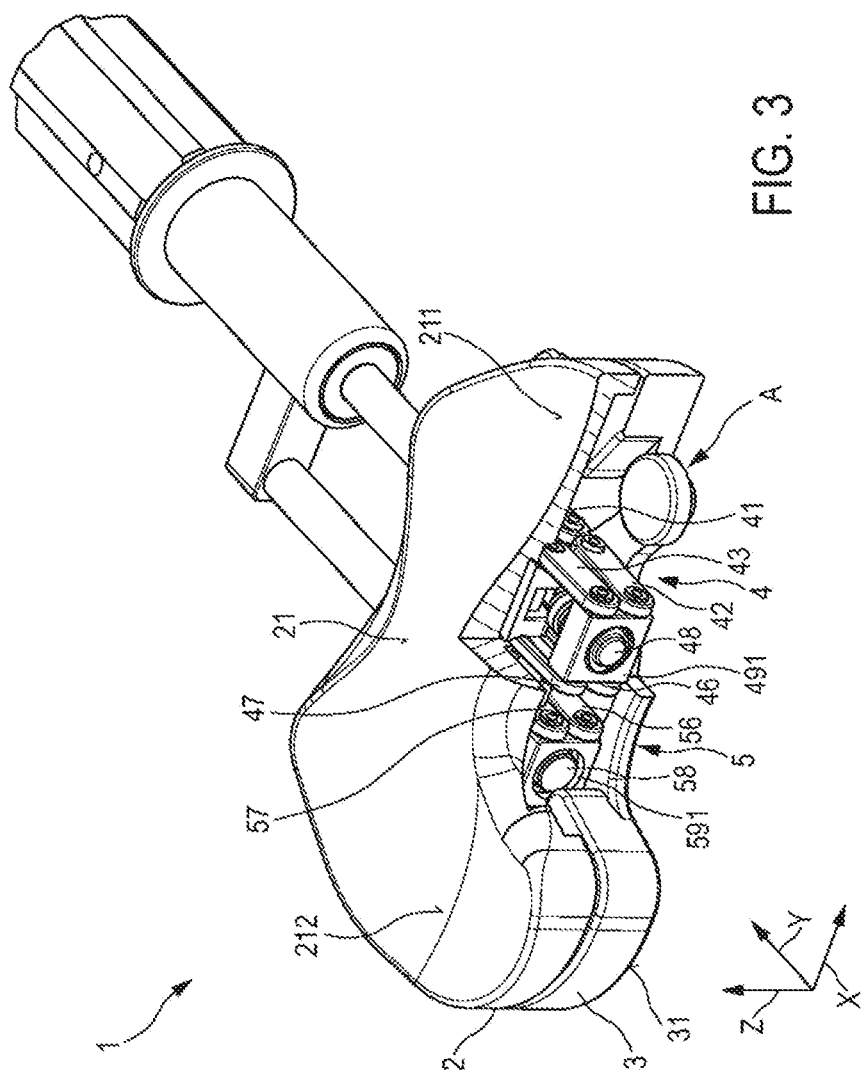
FIG. 3 is the tibial trial insert according to FIGS. 1 and 2 in a partially cut away perspective detail view, wherein the gap between the upper plate and the lower plate is closed.
Figure 4:
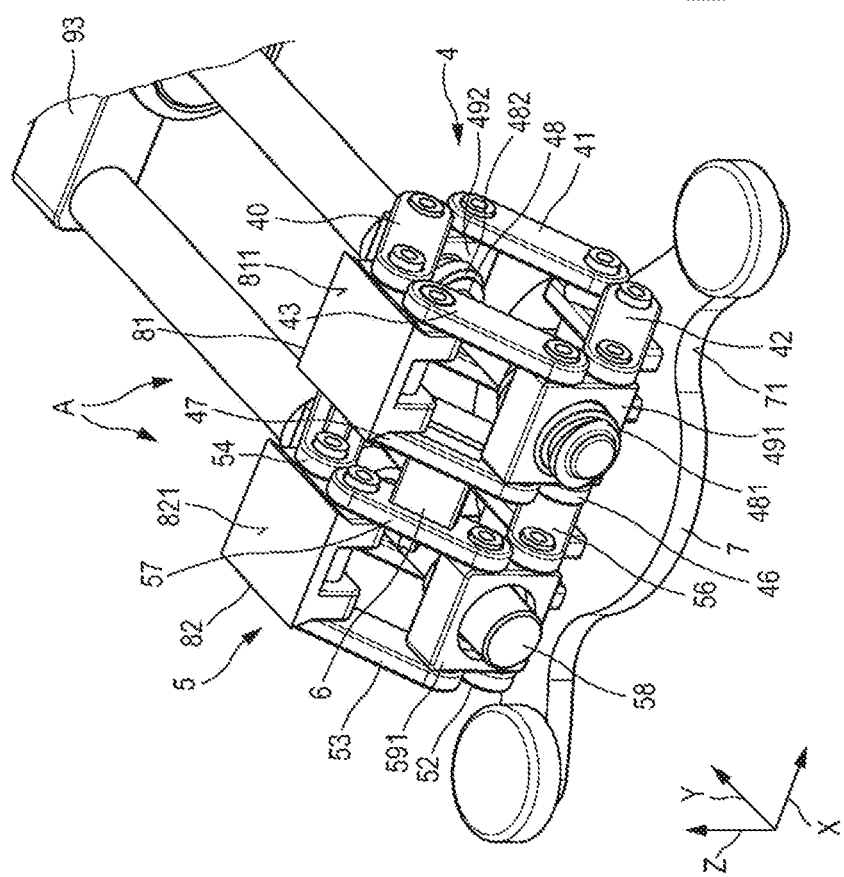
FIG. 4 is the adjustment arrangement of the tibial trial insert according to FIGS. 1 to 3 in a partially cut away perspective view.
Figure 5:
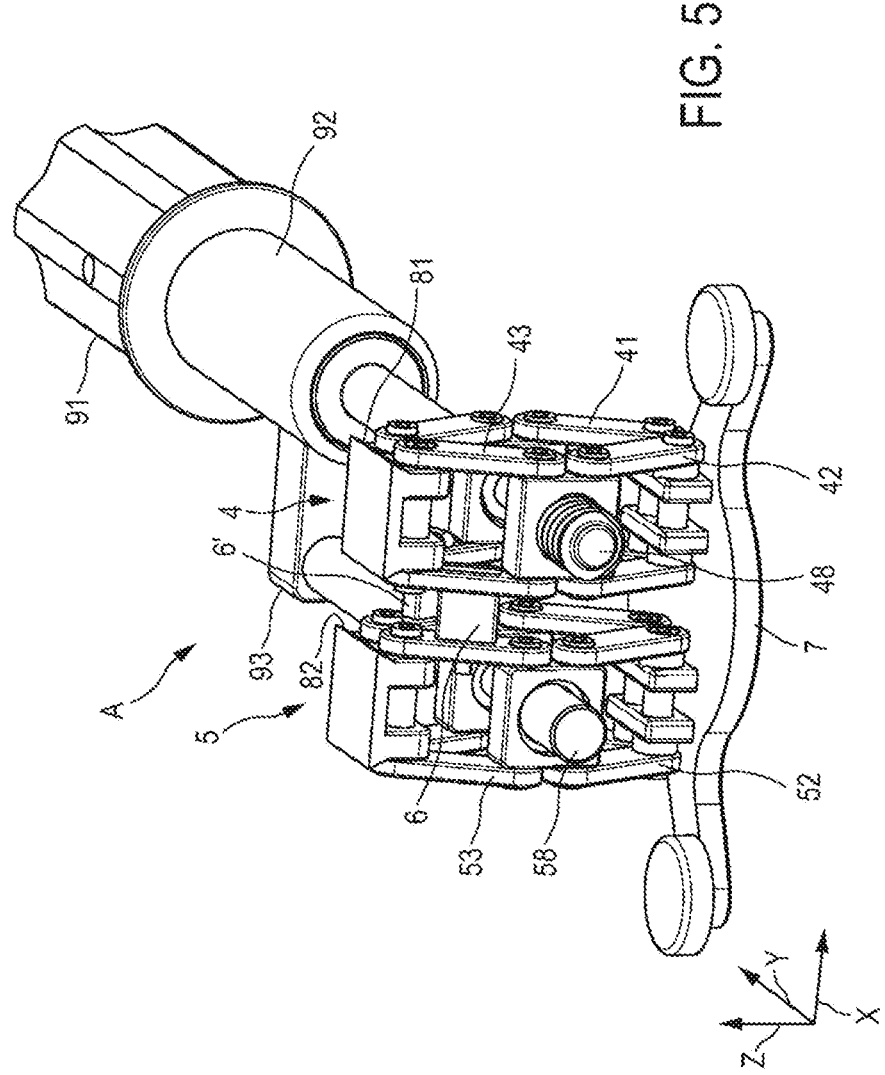
FIG. 5 is a further perspective view of the adjustment arrangement according to FIG. 4.

According to FIGS. 1 to 3, an adjustable tibial trial insert 1 is provided for use in a knee joint replacement surgery. The adjustable tibial trial insert 1 is also referred to as a "trial sliding surface" in medical terminology.

The adjustable tibial trial insert 1 has an upper plate 2, a lower plate 3, and an adjustment arrangement A.

The upper plate 2 is disposed in the vertical direction Z above the lower plate 3, and has an articular surface 21 disposed on the upper side. In the embodiment as illustrated, the articular surface 21 is composed of two partial sliding surfaces 211, 212 which are spaced from each other in the longitudinal direction X by a recess of the upper plate 2, not specified in more detail. The articular surface 21 is provided for sliding interaction with a femoral component. Said femoral component may be a distal end of a femur or a femoral trial implant fixed to said femur with a correspondingly designed sliding surface. The shape configuration of the articular surface 21, as apparent in the Figures, is adapted to the tibial joint surface of a femoral tibial joint in a manner well-known to a person skilled in the art.

The lower plate 3 is disposed in the vertical direction Z below the upper plate 2 and has a lower surface 31 which is provided for tibial fixation. When using the tibial trial insert 1, the lower plate 3 is then disposed and fastened directly or indirectly to a proximal end of a tibia with the lower surface 31 ahead. In the embodiment as illustrated, an indirect fixation of the lower plate 3 is provided, wherein the lower surface 31 interacts with a so-called tibia trial plateau which may be screwed with the proximal end of the tibia or cemented therein.

In the embodiment as illustrated, the upper plate 2 and the lower plate 3 each are plate-shaped such that the respective extension thereof in the longitudinal direction X and in a transverse direction Y are each comparatively greater than an extension thereof in the vertical direction Z.

The adjustment arrangement A is intended for adjusting a gap G extending in the vertical direction Z between the upper plate 2 and the lower plate 3. In other words, the adjustment arrangement A is intended for adjusting an overall height of the tibial trial insert 1 extending in the vertical direction Z. Again put in other words, the upper plate 2 and, thus, the upper articular surface 21 can be positioned in different height levels above the lower plate 2 using the adjustment arrangement A. Such a gap or height adjustment is required for so-called trial reposition in knee joint replacement surgery. The trial reposition is a preceding operation step of the actual knee joint replacement, wherein the dimensions and shapes of the tibial and femoral implant components required for a functional replacement of the knee joint are determined. The application related background of the tibial trial insert 1 is well-known to a person skilled in the art. Therefore, no further explanations are needed in that respect.

The adjustment arrangement A is operatively connected to the upper plate 2 and the lower plate 3 in a manner that will be described in more detail below and thereby allows said relative displacement of the upper plate 3 in relation to the lower plate 2 along the vertical direction Z. With reference to FIGS. 1 and 3, an exemplary illustration of a first adjustment position is given, in which the gap G is closed and the upper plate 2 and the lower plate 3 are disposed directly in superposition. With reference to FIG. 2, an exemplary illustration of a further adjustment position is given, in which the upper plate 2 is lifted by means of the adjustment arrangement A and said gap G is formed.

The adjustment arrangement A is illustrated in detail in particular with reference to FIGS. 4, 5, 6 and 9, and includes a first scissor lift mechanism 4 with a first lever arm arrangement 40 to 47 and a second scissor lift mechanism 5 with a second lever arm arrangement 50 to 57. The two lever arm arrangements 40 to 47 and 50 to 57, respectively, are shown separated for improved clarification with reference to the perspective schematic diagram of FIG. 9. The first lever arm arrangement 40 to 47 and the second lever arm arrangement 50 to 57 are each indirectly connected to the upper plate 2 and the lower plate 3 and are each displaceable between different positions by articulation. In other words, the two scissor lift mechanisms 4, 5 are each extendable and retractable along the vertical axis Z. Again put in other words, a respective length of the two lever arm arrangements 40 to 47 and 50 to 57 is variable along the vertical axis Z in response to the respective articulated displacement position of the lever arm arrangements 40 to 47 and 50 to 57, and thus, finally, also the gap G.

The first scissor lift mechanism 4 comprises an actuator element 48 which is coupled to the first lever arm arrangement 40 to 47 and configured such that actuation of the actuator element 48 varies said length of the first lever arm arrangement along the vertical direction Z. Consequently, actuation of the actuator element 48 causes extending and/or retracting of the first scissor lift mechanism 4.

In contrast thereto, in the embodiment as illustrated, the second scissor lift mechanism 5 does not include a respective actuator element. Rather, the second scissor lift mechanism 5 is coupled to the first scissor lift mechanism 4 by means of at least one coupling element 6 for transmission of force and/or motion such that a length variation of the first lever arm arrangement 40 to 47 is synchronously transmitted to the second lever arm arrangement 50 to 57. Accordingly, the second lever arm arrangement 50 to 57 is force-guided on the first lever arm arrangement 40 to 47 by means of the at least one coupling element 6. In the embodiment as illustrated, a further coupling element 6' is provided for kinematic coupling of the second lever arm arrangement 50 to 57 to the first lever arm arrangement 40 to 47. This feature is advantageous, but not mandatory.

In contrast to separate actuation and adjustment of the two scissor lift mechanisms 4, 5, the above described synchronized adjustment of the length of the second lever arm arrangement 50 to 57 prevents adjustment-related deformations of the articular surface 41 or even damage of the upper plate 2. At the same time, the arrangement of two generally separate scissor lift mechanisms allows improved stability of the tibial trial insert 1, in particular during adjustment of a comparatively large gap size.

Further structural and functional features of the tibial trial insert 1 and the adjustment arrangement A will be discussed below. Said features are advantageous, but not to be considered as required or even essential in view of the implementation of the invention.

The first scissor lift mechanism 4 and the second scissor lift mechanism 5 are spaced apart from each other along the longitudinal axis X. In the present case, the first scissor lift mechanism 4 is disposed below the first partial sliding surface 211 and the second scissor lift mechanism 5 is disposed below the second partial sliding surface 212. In relation to the longitudinal axis X, both the scissor lift mechanisms 4, 5 are disposed in an in-line configuration. Moreover, the two scissor lift mechanisms 4, 5 are disposed in relation to a central longitudinal plane of the upper plate 2, extending in the vertical and transverse directions, which may also be referred to as central plane C.

In the embodiment as illustrated, the two scissor lift mechanisms 4, 5 furthermore have—with the exception of the presence or absence of the actuator element 48—an identical design, in relation to configuration and dimensions, in particular of the lever arm arrangements 40 to 47 and 50 to 57, and to that extent are composed using common parts. Thereby, in particular specifically simple and cost-efficient manufacture and assembly can be achieved.

Figure 9:
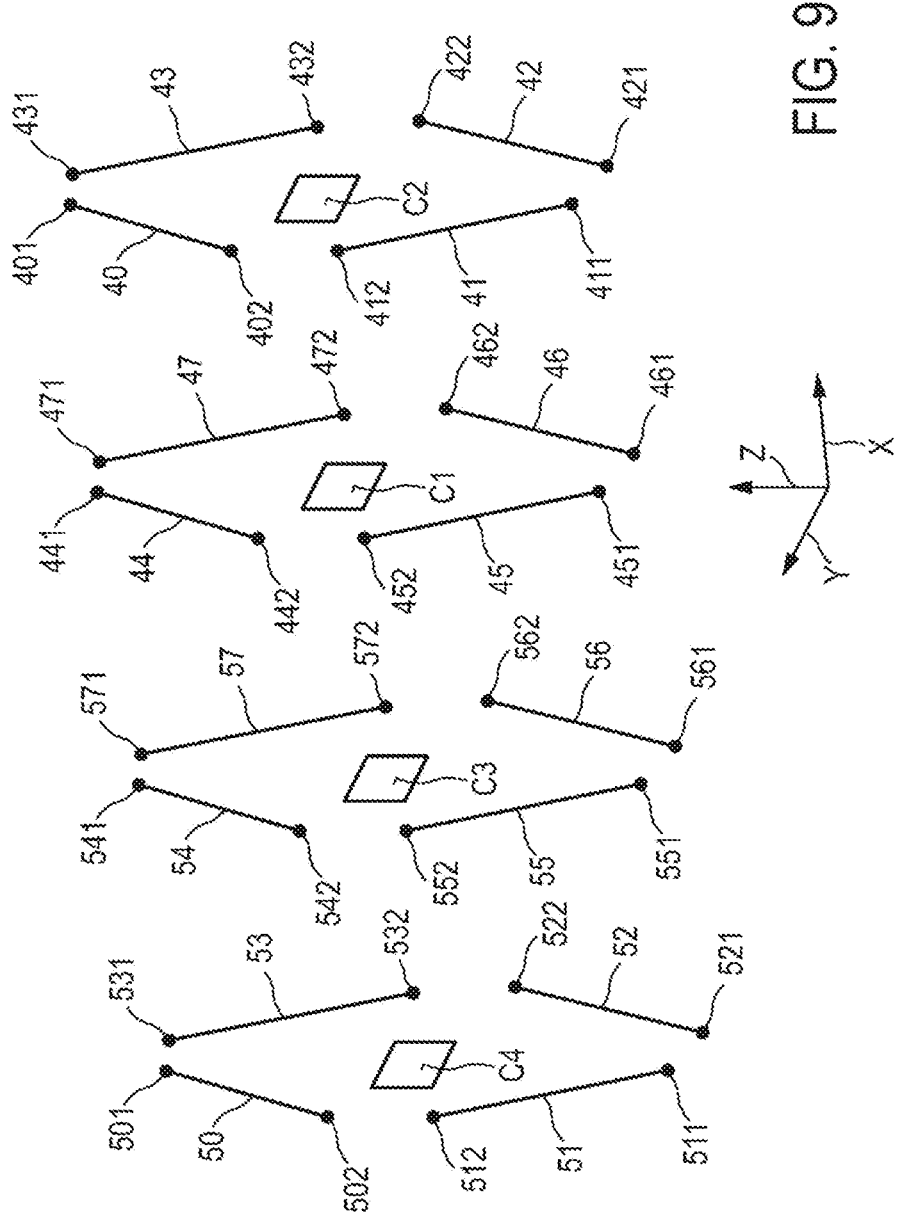
FIG. 9 is a schematic illustration showing the arrangement of individual components of the adjustment arrangement in a perspective view, corresponding approximately to the perspective of FIG. 5.

In particular with reference to FIG. 9, it is apparent in detail that the first lever arm arrangement 40 to 47 and the second lever arm arrangement 50 to 57 each include a plurality of inner lever arms 44 to 47 and 54 to 57, respectively, and a plurality of outer lever arms 40 to 43 and 50 to 53, respectively. Said lever arms may also be referred to as first outer lever arms 40 to 43, first inner lever arms 44 to 47, second outer lever arms 50 to 53, and second inner lever arms 54 to 57. The inner and outer lever arms are offset in relation to the longitudinal axis X and/or spaced from each other and, thus, disposed in different planes. The first inner lever arms 44 to 47 are disposed in a plane C1; the first outer lever arms 40 to 43 are disposed in another plane C2; the second inner lever arms 54 to 57 are disposed in another plane C3; the second outer lever arms 50 to 53 are disposed in another plane C4. The planes C1 to C4 are schematically illustrated in FIG. 9 and each extend in the vertical direction Z and transverse direction Y and parallel to each other. The lever arms 40 to 57 are pivotable in their respective plane C1 to C4 such that they also may be referred to as pivot planes C1 to C4.

In the embodiment as illustrated, each of the two lever arm arrangements 40 to 47 and 50 to 57 are respectively composed of exactly eight lever arms, wherein in each case four inner and four outer lever arms are provided. The first lever arm arrangement 40 to 47 is symmetrical in relation to a horizontal central plane (not specified in more detail) extending in the transverse direction Y and the longitudinal direction X. The same applies to the second lever arm arrangement 50 to 57. In relation to said horizontal central plane and the vertical direction Z, respectively, the lever arms may also be referred to as upper lever arms 40, 43, 44, 47, 50, 53, 54, 57 and lower lever arms 41, 42, 45, 46, 51, 52, 55, 56. All of the above described lever arms have a lengthwise extension in their corresponding allocated plane C1 to C4 between a first end and a second end. In FIG. 9 reference is made to the respective first and second ends in that the reference numeral of the corresponding lever arm has the digit 1 or 2 added thereto. Accordingly, the inner upper lever arm 44 of the first lever arm arrangement 40 to 47 comprises a first end 441 and a second end 442. Correspondingly, the lower outer lever arm 52 of the second lever arm arrangement 50 to 57 comprises a first end 521 and a second end 522. The designation of the first and second ends of the further lever arms, in particular apparent in FIG. 9, is analogous so that the reference numerals are not each explained in detail.

The first ends 411, 421, 451, 461, 511, 521, 551, 561 of the lower lever arms 41, 42, 45, 46, 51, 52, 55, 56 are each at least indirectly mounted on the lower plate 3 for pivot movement. In the present case, the adjustment arrangement A comprises, for that purpose, a lower supporting plate 7 which, in turn, is connected to the lower plate 3 in a manner that will be described in more detail below. In a not illustrated embodiment, said first ends of the lower lever arms may instead be mounted directly on the lower plate for pivot movement.

The first ends 401, 431, 441, 471, 501, 531, 541, 571 of the upper lever arms 40, 43, 44, 47, 50, 53, 54, 57 are each at least indirectly mounted on the upper plate 2 for pivot movement. In the embodiment as illustrated, the adjustment arrangement A comprises, for that purpose, supporting elements 81, 82 which, in turn, are connected to the upper plate 2 in a manner that will be described in more detail below. In a not illustrated embodiment, said first ends of the upper lever arms may instead be mounted directly on the upper plate for pivot movement.

The two scissor lift mechanisms 4, 5 each comprise a first coupling block and a second coupling block, on which the respective second ends of the lever arms are mounted for pivot movement. In detail, the first scissor lift mechanism 4 comprises a first coupling block 491 and a second coupling block 492. The second scissor lift mechanism 5 correspondingly comprises a first coupling block 591 and a second coupling block 592. The coupling blocks 491, 492 are disposed in the longitudinal direction X between the inner lever arms 44 to 47 and the outer lever arms 40 to 43 of the first scissor lift mechanism 4. The coupling blocks 591, 592 of the second scissor lift mechanism 5 are disposed in relation to the longitudinal direction X between the inner lever arms 54 to 57 and the outer lever arms 50 to 53. The first coupling block 491 and the second coupling block 492 are spaced apart from each other in the transverse direction Y. The same applies correspondingly to the two coupling blocks 591, 592. The coupling blocks 491, 492, 591, 592 are intended in particular for pivotable mounting of the second ends 402, 412, 422, 432, 442, 452, 462, 472, 502, 512, 522, 532, 542, 552, 562, 572 of the lever arms 40 to 47 and 50 to 57. The Figures illustrate directly and unambiguously which one of the two ends is mounted on which one of the coupling blocks, therefore, a literal description of the disclosure in the drawings is unnecessary.

In the embodiment as illustrated, the actuator element 48 is a threaded bolt and comprises a first threaded portion 481 and a second threaded portion 482. The threaded portions 481, 482 are configured in mutually opposite directions. The first threaded portion 481 interacts with a complementary threaded hole of the coupling block 491 (not specified in more detail). The second threaded portion 482 interacts with a complementary threaded hole of the second coupling block 492 (not specified in more detail). The actuator element 48 extends lengthwise between the threaded portions 491, 492, in parallel to the transverse axis Y.

The coupling elements 6, 6' each extend lengthwise, in parallel to the longitudinal axis X. The coupling element 6 is on one end fixedly connected to the inner upper lever arm 47 of the first lever arm arrangement 40 to 47 and on the other end fixedly connected to the inner upper lever arm 57 of the second lever arm arrangement 50 to 57. The second coupling element 6' is on one end fixedly connected to the lever arm 44 and on the other end fixedly connected to the lever arm 54. The coupling elements 6, 6' cause transmission of force and, thus, also of motion from the first lever arm arrangement 40 to 47 to the second lever arm arrangement 50 to 57.

Moreover, the adjustment arrangement A comprises a guiding bolt 58 which slidingly cooperates with the first coupling block 591 and the second coupling block 592 of the second scissor lift mechanism 5 along the transverse axis Y. Simply put, the guiding bolt 58 is provided in the second scissor lift mechanism 5 instead of the actuator element 48 of the first scissor lift mechanism 4. The guiding bolt 58 cooperates with cylindrical bolt seats of the coupling blocks 591, 592 (not specified in more detail), and serves for kinematic guide and/or support of the second lever arm arrangement 50 to 57. The guiding bolt 58 extends lengthwise in parallel to the transverse axis Y.

In the embodiment as illustrated, the adjustment arrangement A moreover comprises a handle 9 with a manipulation element 91. The manipulation element 91 is operatively connected to the actuator element or threaded bolt 48 for transmission of force and motion, and in the present case configured as a cylindrical rotary actuation element which is provided with radial grooves spaced in the peripheral direction (not specified in more detail). The handle 9 has a cylindrical shaft 92 extending lengthwise and in parallel to the transverse axis Y. The manipulation element 91 is mounted on one end to the shaft 92 for rotation about the transverse axis Y. A protrusion (not specified in more detail) of the actuator element 48 projects into the shaft 92 along the transverse direction Y and is therein operatively connected to the manipulation element 91 in a manner well-known to a person skilled in the art.

The guiding bolt 58 extends lengthwise between a first portion 581 and a second portion 582. The first portion 581 cooperates in said manner with the coupling blocks 591, 592 in sliding movement along the transverse direction Y. The second portion 582 is operatively connected to the handle 9. For that purpose, in the present case, the second portion 582 is connected to a connector element 93 which projects from the shaft 92 in the radial direction and is fixed to said shaft.

Figure 6:
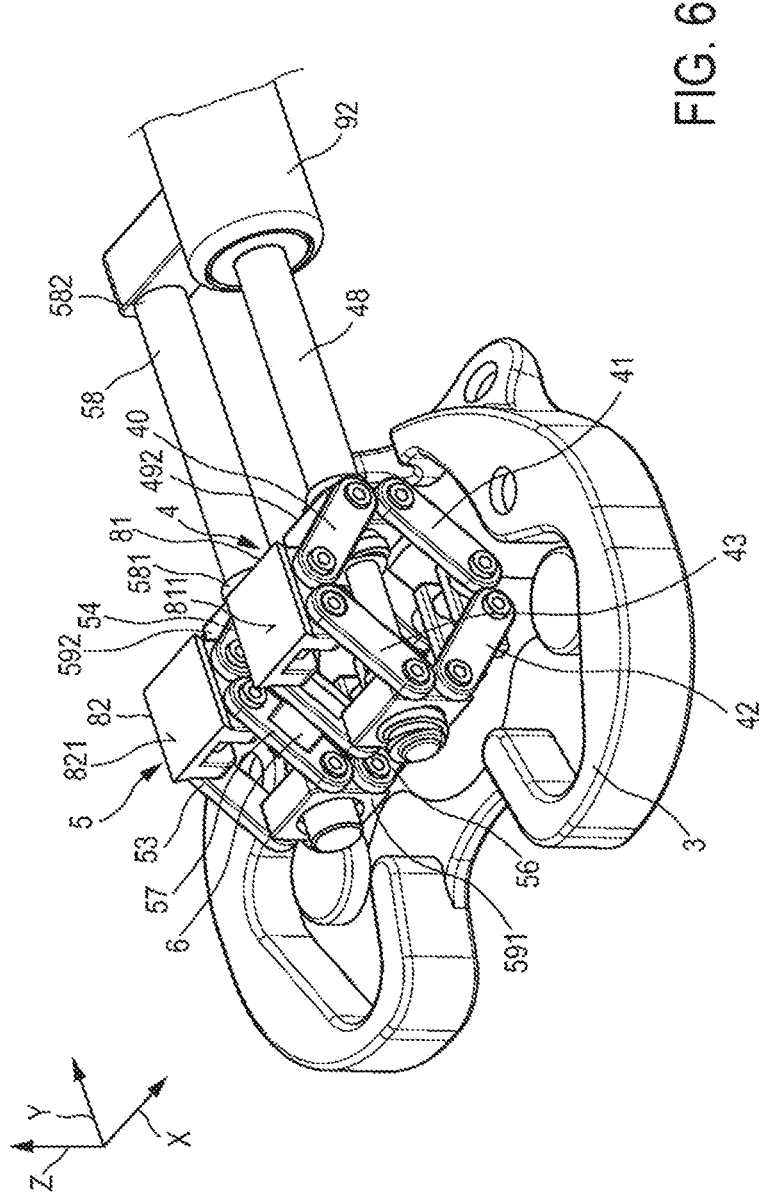
FIG. 6 is a further partially cut away perspective view of the tibial trial insert with graphical suppression of the upper plate.
Figure 7:
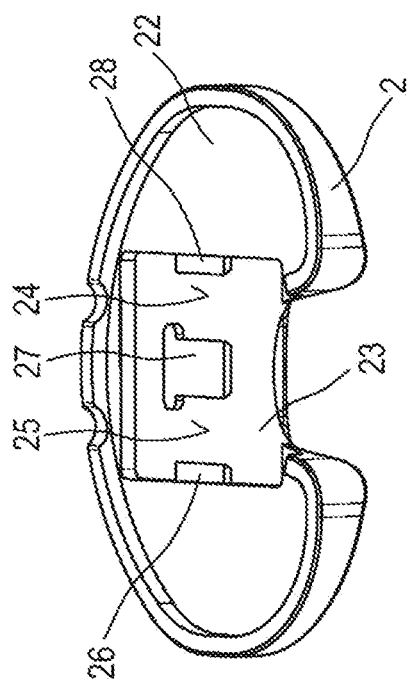
FIG. 7 is a perspective detail view of the upper plate with a direction of view to a lower side.
Figure 8:
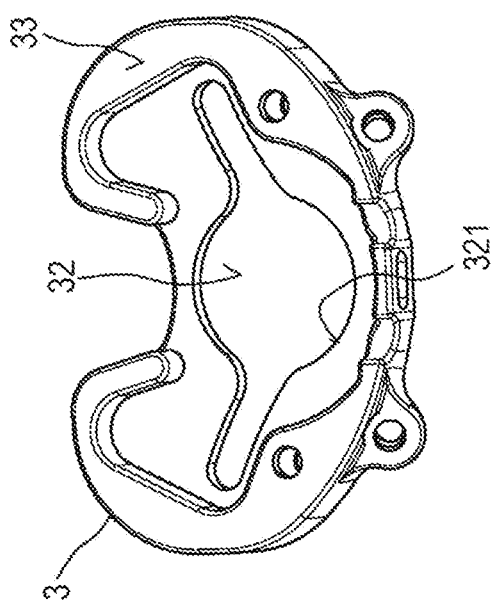
FIG. 8 is a perspective detail view of the lower plate with a direction of view to an inner side.

The connection between the handle 9 and the actuator element 48 and the guiding bolt 58 can be permanent or detachable, wherein in particular FIG. 6 shows a permanent connection. Alternatively, the variant according to FIG. 10 shows a detachable connection between the handle 9a and the remaining parts of the adjustment arrangement. The detachable connection is established by means of torque-transmitting plug connections between hexagon sockets 921', 931' and hexagon heads 921, 931. The hexagon head 921 is rotatably mounted to the cylindrical shaft 92a, can be plugged into the hexagon socket 921' of the actuator element 48, and is rotatable by turning the manipulation element 91. The hexagon head 931 is fixedly mounted to the connector element 93a, and can be plugged into the hexagon socket 931' of the guiding bolt 58.

For connection of the adjustment arrangement A to the upper plate 2, the supporting elements 81, 82 comprise separate connector portions 811 and 821, respectively. The connector portions are detachably connectable in a form-fitting manner with complementary connector portions 24, 25 of the upper plate 2. The complementary connector portions 24, 25 are disposed on an inner side 22 facing the lower plate 3 and, in the present case, provide sections of a recess 23 countersunk in the inner side 22 along the vertical axis Z. In the region of the recess 23, a plurality of form elements 26, 27, 28 are disposed, which cooperate releasably with the connector portions 811, 821 in a form-fitting manner. The lower supporting plate 7 comprises, in the present case, an outer contour 71 which is utile as a connector portion for releasable form-fitting connection to a complementary connector portion 32 of the lower plate 3. The complementary connector portion 32 has an inner contour 321 which is complementary to the outer contour 71 of the lower plate 7. The connector portion 32 of the lower plate 3 is disposed on an inner side 33 facing the upper plate 2.

Owing to the releasable form-fitting connectability of the adjustment arrangement A to the upper and the lower plates 2, 3, a modular construction of the adjustable tibial trial insert 1 is achieved. Said modular construction allows that the adjustment arrangement A can be connected to upper and/or lower plate of different configuration, depending on the medical conditions in a knee joint replacement surgery operation, as required.

For adjustment of the gap G, the actuator element 48 is rotated about its longitudinal axis by means of rotary actuation of the manipulation element 91. As a result, the actuator element 48 interacts with the coupling blocks 491, 492 of the first scissor lift mechanism 4 via the threaded portions 481, 482 in threaded motion. As a consequence of the opposite configuration of the threaded portions 481, 482, the coupling blocks 491, 492 are thereby displaced relative to each other along the transverse axis Y in translational move. The effect thereof is that the second ends of the lever arms of the first lever arm arrangement 40 to 47, pivotally mounted on the coupling blocks 491, 492, are moved towards each other or away from each other in translation along the transverse axis Y. Consequently, the distance of the first ends of the lever arms of the first lever arm arrangement 40 to 47 is inevitably also varied such that the length of the lever arm arrangement 40 to 47 in relation to the vertical axis Z is varied. In other words, the first scissor lift mechanism 4 is extended and/or retracted thereby. The second scissor lift mechanism 5 is moved correspondingly thereby, by means of the coupling elements 6, 6' in forced guiding such that the length of the second lever arm arrangement 50 to 57 varies in synchronization with the first lever arm arrangement 40 to 47. As a result of the upper-sided and lower-sided support of the adjustment arrangement A via the supporting elements 81, 82 and the lower supporting plate 7, finally, the gap G between the upper plate 2 and the lower plate 3 is varied in response to the retracting and extending movement, respectively, of the scissor lift mechanisms 4, 5.

The invention claimed is:

1. An adjustable tibial trial insert, comprising:
an upper plate including an upper articular surface configured for articulation with a femoral surface;
a lower plate positioned below the upper plate along an adjustment axis and including a lower surface configured for tibial fixation; and
an adjustment arrangement arranged between the upper plate and the lower plate and actuatable for adjustment of a gap between the upper plate and the lower plate along the adjustment axis,
the adjustment arrangement comprising at least a first scissor lift mechanism with a first lever arm arrangement and a second scissor lift mechanism with a second lever arm arrangement, the second scissor lift mechanism being separate from the first scissor lift mechanism,
each of the first and second lever arm arrangements being indirectly connected to the upper plate and the lower plate,
each of the first and second lever arm arrangements comprising a length and being pivotally movable between different positions for variation of said length along the adjustment axis to adjust the gap between the upper plate and the lower plate,
the first scissor lift mechanism comprising an actuator element coupled to the first lever arm arrangement and configured such that actuation of the actuator element varies the length of the first lever arm arrangement, and
the adjustment arrangement comprising at least one coupling element coupling the second scissor lift mechanism to the first scissor lift mechanism and configured such that the length of the second lever arm arrangement is varied synchronously to the first lever arm arrangement,
wherein each of the first and second lever arm arrangements comprises a plurality of inner lever arms and a plurality of outer lever arms, wherein the inner lever arms are disposed and pivotally movable in a first plane whose normal vector is oriented perpendicular to the adjustment axis, and wherein the outer lever arms are disposed and pivotally movable in a second plane spaced parallel to the first plane,
wherein each of the plurality of inner lever arms and each of the plurality of outer lever arms comprises four lever arms including two upper lever arms and two lower lever arms positioned below the two upper lever arms along the adjustment axis,
wherein each of the upper lever arms extends from a first end to a second end, said first end being pivotally coupled to the upper plate,
wherein each of the lower lever arms extends from a third end to a fourth end, said third end being pivotally coupled to the lower plate,
wherein each of the first and second scissor lift mechanisms comprises a first coupling block and a second coupling block, each of the first and second coupling blocks being disposed between the first plane and the second plane, wherein the second ends of the upper lever arms are coupled to one of the first coupling blocks, and the fourth ends of the lower lever arms each are pivotally coupled to one of the second coupling blocks, and
wherein the actuator element is threadably connected to the first coupling block and the second coupling block of the first scissor lift mechanism along a transversal axis that is perpendicular to the adjustment axis such that actuation of the actuator element translates the first and second coupling blocks relative to each other to vary the length of the first lever arm arrangement, wherein variation of the length of the first lever arm arrangement is synchronously transmitted to the second lever arm arrangement by the coupling element.

2. The adjustable tibial trial insert according to claim 1, wherein the first scissor lift mechanism and the second scissor lift mechanism are spaced apart from each other along a longitudinal axis, wherein the longitudinal axis is oriented perpendicular to the adjustment axis.

3. The adjustable tibial trial insert according to claim 1, wherein the first scissor lift mechanism and the second scissor lift mechanism are arranged in an in-line configuration and/or are arranged symmetrically with respect to a center plane of the upper plate.

4. The adjustable tibial trial insert according to claim 1, wherein the at least one coupling element extends from a first end to a second end, wherein the first end is coupled to a first lever of the first lever arm arrangement and the second end is coupled to a second lever of the second lever arm arrangement.

5. The adjustable tibial trial insert according to claim 1, wherein the adjustment arrangement comprises an upper connector portion for releasable form-fitting connection with a complementary connector portion of the upper plate and a lower connector portion for releasable form-fitting connection with a complementary connector portion of the lower plate.

6. The adjustable tibial trial insert according to claim 1, wherein the adjustment arrangement comprises a guiding bolt slidably connected to the first coupling block and the second coupling block of the second scissor lift mechanism along the transversal axis such that the first coupling block and the second coupling block of the second scissor lift mechanism are supported on the guiding bolt.

7. The adjustable tibial trial insert according to claim 6, wherein the adjustment arrangement comprises a handle having a manipulation element operatively connected to the actuator element such that manipulation of the manipulation element actuates the actuator element to vary the length of the first and second lever arm arrangements in order to vary the gap between the upper plate and the lower plate.

8. The adjustable tibial trial insert according to claim 7, wherein the guiding bolt has a first portion slidably connected to the first coupling block and second coupling block of the second scissor lift mechanism and a second portion operatively connected to the handle.

9. The adjustable tibial trial insert according to claim 7, wherein the handle is detachably connected to the actuator element and/or the guiding bolt.

* * * * *